(12) United States Patent
Starostovic et al.

(10) Patent No.: US 6,505,129 B2
(45) Date of Patent: Jan. 7, 2003

(54) PANEL TESTER AND GRADER

(75) Inventors: Edward J. Starostovic, Stoughton, WI (US); Justin M. Janisch, Stoughton, WI (US)

(73) Assignee: Timberco, Inc., Madison, WI (US)

( * ) Notice: Subject to any disclaimer, the term of this patent is extended or adjusted under 35 U.S.C. 154(b) by 0 days.

(21) Appl. No.: 10/123,880

(22) Filed: Apr. 16, 2002

(65) Prior Publication Data

US 2002/0173921 A1 Nov. 21, 2002

Related U.S. Application Data

(63) Continuation-in-part of application No. 09/431,865, filed on Nov. 2, 1999, now Pat. No. 6,381,546.

(51) Int. Cl.[7] .................................................. G01N 3/20
(52) U.S. Cl. .............................. 702/36; 702/97; 73/849
(58) Field of Search ............................. 702/36, 41, 42, 702/113, 91, 94, 97; 73/849, 851, 852; 428/119, 120

(56) References Cited

U.S. PATENT DOCUMENTS

| 4,589,288 A | 5/1986 | Porter et al. |
|---|---|---|
| 4,708,020 A | 11/1987 | Lau et al. |
| 4,852,029 A | 7/1989 | Pope et al. |
| 5,060,516 A | 10/1991 | Lau et al. |
| 5,231,882 A | 8/1993 | Bertele |
| 5,503,024 A | 4/1996 | Bechtel et al. |
| 5,699,274 A | 12/1997 | Starostovic, Jr. |
| 5,804,738 A | 9/1998 | Bach et al. |
| 6,053,052 A | 4/2000 | Starostovic |
| 6,055,867 A | 5/2000 | Dunne et al. |
| 6,381,546 B1 * | 4/2002 | Starostovic ................. 428/119 |

* cited by examiner

Primary Examiner—Kamini Shah
(74) Attorney, Agent, or Firm—Teresa J. Welch; Thomas S. Reynolds, II; Michael Best & Friedrich LLP

(57) ABSTRACT

A panel tester and grader includes a main frame including a plurality of rollers and defining a substantially S-shaped testing path. A substantially linear bypass path extends below the testing path and a bypass assembly is coupled to the main frame and is operable to move the main frame between a testing position in which panels are received by the testing path, and a bypass position in which panels are received by the bypass path. A load cell providing a load output is coupled to a deflector roller to measure a load applied to the panel by the deflector roller. The load output is monitored as the panels are guided through the panel tester and the load output is selectively recorded based upon the monitored load output.

19 Claims, 2 Drawing Sheets

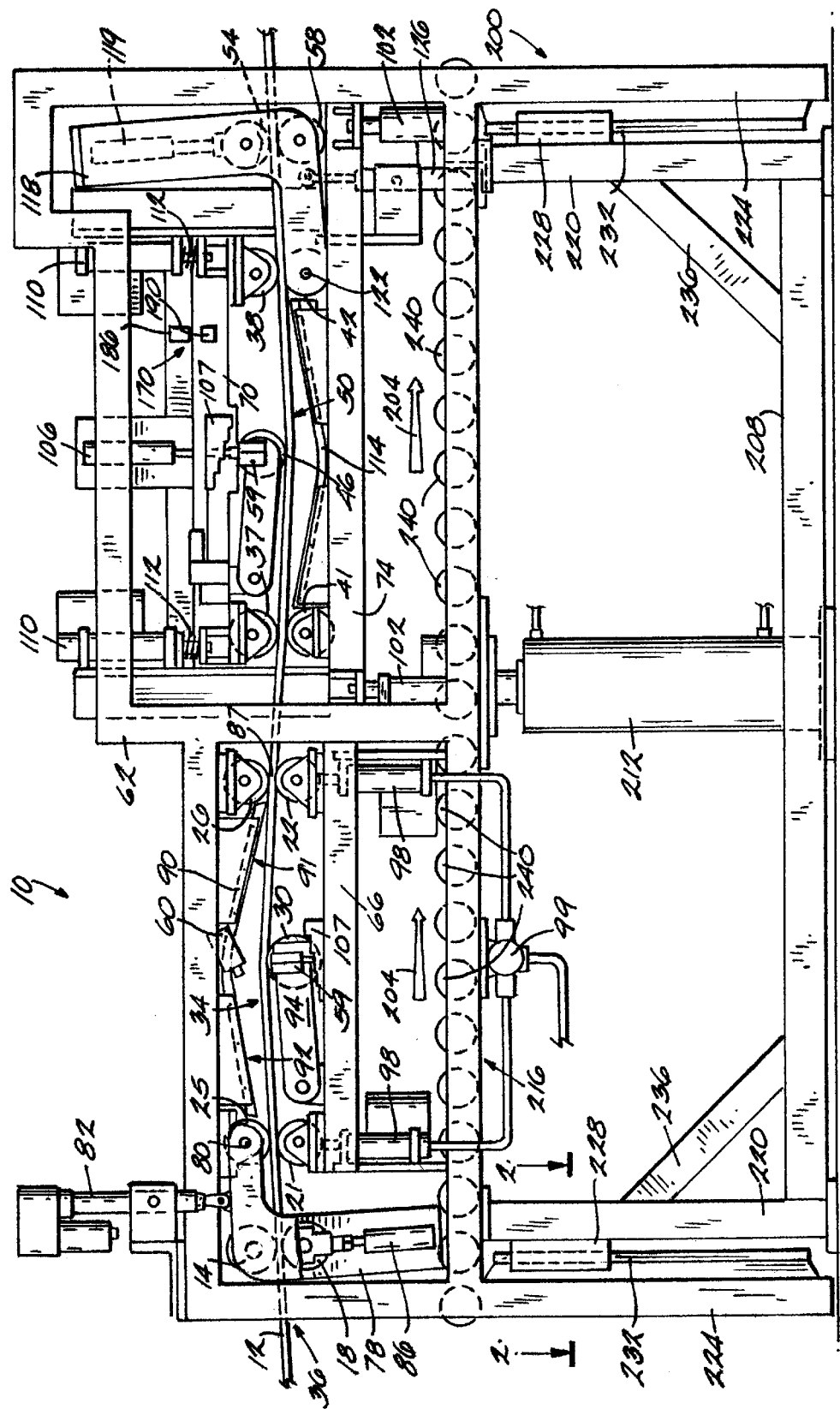

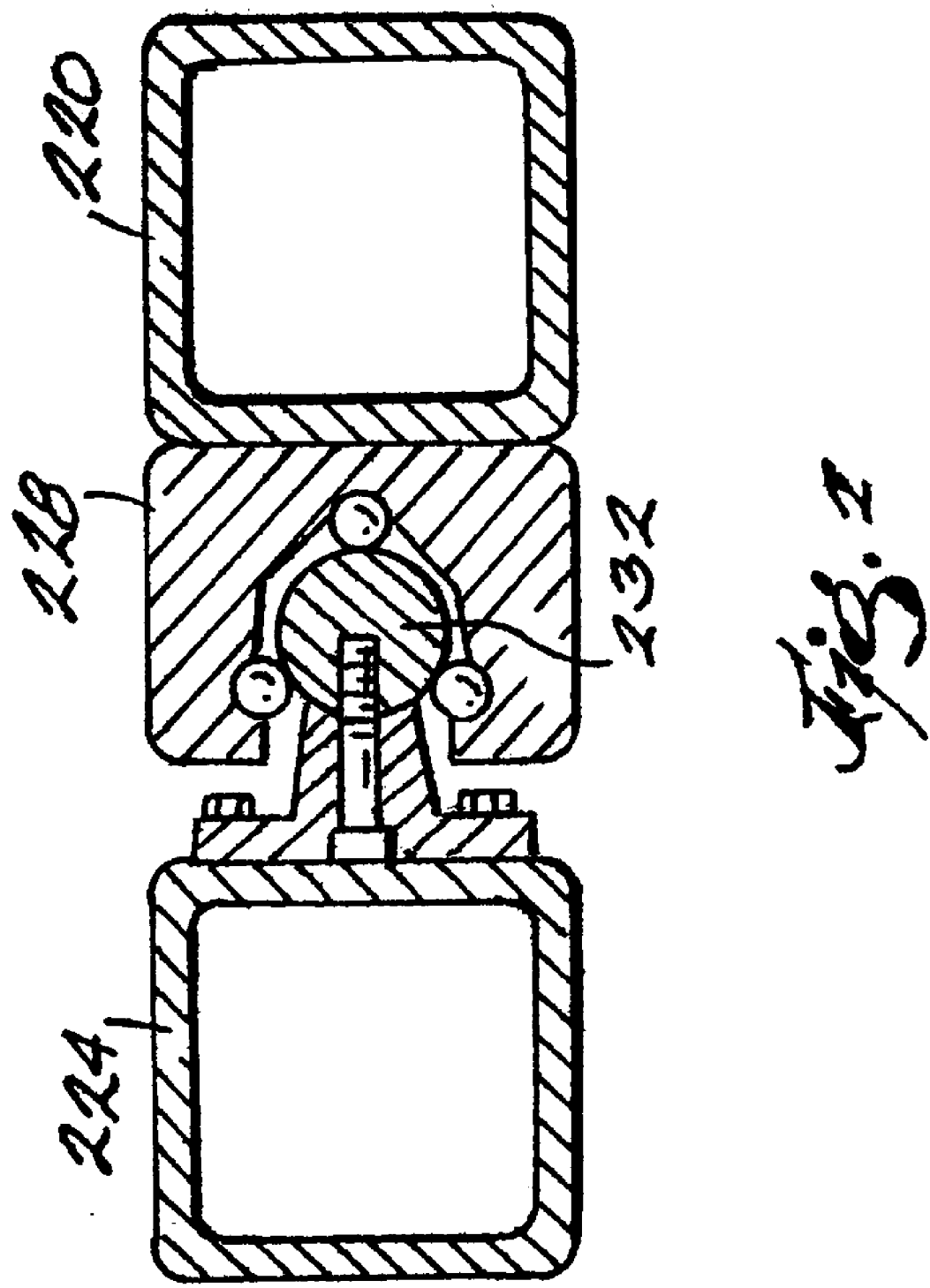

PANEL TESTER AND GRADER

PRIORITY INFORMATION

The present application is a continuation-in-part of U.S. patent application Ser. No. 09/431,865, filed Nov. 2, 1999 now U.S. Pat. No. 6,381,546.

FIELD OF THE INVENTION

The present invention relates generally to nondestructive testing of composite materials or panels, particularly wood based materials, such as plywood, oriented strand board, wafer board, particle board, and the like, to determine the strength and stiffness of such panels.

BACKGROUND OF THE INVENTION

The use and acceptance of composite materials and panels for various applications, such as, building constructions, continues to increase in the market place. As a result, it is becoming increasingly desirable to monitor the strength and stiffness of the panels being produced. This is so because the strength and stiffness of composite materials varies greatly due to the composite nature of the products and the difficulty in achieving uniform strength in the bonding materials used to join the composites together. Moreover, variations in feedstocks and other factors make manufacture of uniformly strong and elastic structures from composite elements difficult and costly.

Nondestructive inspection and testing of materials of all sorts is known. Many of the known methods for performing certain standards tests are manual or static methods. For example, to conduct a concentrated load test, it is known to build a frame with beams simulating joists in a building construction. The beams are spaced apart depending upon the end use and span rating of the panel to be tested. A hydraulically-actuated load is applied to the stationary panel at a specified distance from a non-secured edge and the deflection of the panel is measured by placing a dial-micrometer under the panel at a position opposite the load and reading the deflection on the micrometer scale.

U.S. Pat. No. 4,708,020 to Lau et al., which is incorporated herein by reference, relates to another form of nondestructive inspection and testing of composite panels to determine the strength and stiffness of the panels. More particularly, Lau et al. provide an apparatus and process for correlating end-use strength and stiffness values when the testing is carried out on hot panels. The panels may be tested at one temperature, approaching the press temperature, and the strength and stiffness determined for the end products at another temperature, generally ambient or end-use temperature. Lau et al. also provide a testing machine suitable for in-line testing for determining the strength and stiffness of panel products having different thicknesses. The testing machine of Lau et al. also enables panels to be graded so that rejects can be identified and panels can be separated into grade groups representing different strength and stiffness ranges.

The continuous panel tester of Lau et al. imposes a double reverse bend or "S" shaped configuration on the panels as they pass through the conveyor at line speed. The device of Lau et al. is configured and operated such that either the deflection of each panel may be measured for a specific load, or the load is measured for a particular deflection of each panel.

As set forth in Lau et al., there is provided a first in-feed roll and a last out-feed roll to direct each panel to be tested into and out of the overall continuous panel tester and grader. As also described in Lau et al., a plurality of photo switches along the conveyor line have the function of informing the microprocessor when a panel is in the tester. The photo switches of Lau et al. determine when one panel ends and a second panel commences to pass through the tester so as to ensure that readings from the load cells and temperature sensor represent strength and stiffness figures for one panel. Another feature of Lau et al. is the ability of the panel grader to test panels having different thicknesses by merely selecting the required nominal panel thickness. The microprocessor is programmed to control the necessary equipment to position the rolls of the apparatus to process the panels of the selected nominal thickness. Based on the selected nominal thickness which is inputted to the microprocessor, the microprocessor utilizes information received from the load cells and temperature sensor to calculate the hot strength and stiffness values for each panel and then the microprocessor uses a preprogrammed algorithm to determine the ambient or cold end-use strength and stiffness value for each of the tested panels. Lau et al. do provide that it may be desirable to use a thickness measuring sensor such as a laser sensor or an ultrasonic sensor, which is placed near the in-feed rolls of the panel tester, to obtain a more actual thickness measurement of each panel, as compared to using the selected nominal thickness for each panel, thereby providing for a more accurate calculation of the strength and stiffness properties for each panel.

Despite the increased use of composite materials for all sorts of building constructions and other uses, and the general desire to test the composite materials for strength and stiffness, a need still exists for an improved panel tester and grader which is efficient and economical in its manufacture and use and which also provides improved accuracy in terms of measuring and grading panel like products according to desired strength and stiffness values.

As can be appreciated by those skilled in the art, the many known manual methods for performing certain standard tests for panels or the like are generally labor intensive, slow processing, somewhat costly procedures that can readily lead to error or operator mistakes when trying to determine the strength and stiffness values for panels. Moreover, the known static testing machines do not allow a panel to continually move along the production line during testing, thereby limiting the usefulness of such testing equipment.

Although Lau et al. describe an automatic, continuous panel tester and grader which is in many aspects an improvement over the known manual or static methods, the device of Lau et al. also exhibits several problems. One problem with Lau et al. concerns the bending forces that are applied to the panels as they are fed to and passed out of the panel tester. Although Lau et al. recognize that no significant forces should be applied to the panels that would distort the loading forces of the panels in the "S" shaped path, it has actually been determined according to the present invention that the first in-feed roller (40) and the last out-feed roller (70) of Lau et al. (see FIG. 2 thereof) do in fact apply undesirable bending forces or moments to the panels as they travel thereover, thereby resulting in significantly less than accurate strength and stiffness values for the tested panels. It has been determined according to the present invention that if the panels are subjected to a bending force outside the critical load zone or path, the deflection for a specific load or the load applied for a particular deflection may be greater than or less than what the actual deflection or load would be absent the undesirable bending force, depending on the direction the panels are caused to bend outside the load zone.

Another problem with Lau et al. concerns the location of the photo switches (1)–(4) (see FIG. 1 thereof) which communicate with the microprocessor (22) so that the microprocessor knows when to begin and when to end taking and recording loading and temperature readings for a specific panel traveling through the panel tester. Lau et al. disclose that a composite panel (10) moves in an "S" shaped path through the tester. The first deflector roll (14) is positioned midway between a first pair of spaced positioning rolls (13) each of which cooperates with its respective reaction roll (50) to clamp the panel (10) therebetween, all of which function to bend the panel in a first direction in the first curved portion of the "S" shaped path. The second deflection roll (16) is positioned substantially midway between a second pair of positioning rolls (13) each of which cooperates with its respective reaction roll (60) to clamp the panel (10) therebetween, all of which function to bend the panel in a second direction opposite to the first direction in the second curved portion of the "S" shaped path, i.e., in a reverse curvature to that forced by the first deflection roll (14). According to Lau et al., when the photo switches indicate that a panel is in the tester, readings from the load cells (18) and temperature sensor (24) are taken at predetermined intervals and the microprocessor uses these readings to calculate a strength and stiffness value for each panel tested. As shown and described in Lau et al., the photo switches are placed along the processing line with no particular regard as to how their placement may affect the calculated strength and stiffness values. In other words, what Lau et al. fail to recognize, and what has been determined according to the present invention, is that the location of the photo switches or sensors relative to the load zone of the "S" shaped path is important in terms of the overall calculated strength and stiffness value for each panel tested.

According to the present invention, it has been determined that in order to compute more accurate strength and stiffness values for the panels, each panel should be subjected to bending forces in the first and second curved portions of the "S" shaped path or load zone between the pairs of opposed positioning and reaction rolls adjacent to the respective deflector rolls. Any forces or adverse bending moments applied to the panels outside the load zone which causes the panels to bend in an undesirable manner, will result in less than accurate strength and stiffness values. Accordingly, since the panels should only be subjected to the appropriate bending forces within the load zone, and since the microprocessor calculates a strength and stiffness value for each panel traveling through the panel tester, it is desirable for the microprocessor to take and record the desired measurement readings only when each panel is in or substantially in the load zone of the "S" shaped path as defined between the pairs of opposed positioning and reaction rolls. Locating the photo switches as illustrated in Lau et al. results in the microprocessor taking and recording the load and temperature readings for the panels when the panels are not properly in the defined load zone of the "S" shaped path, thereby undesirably skewing the calculated strength and stiffness values for the panels.

Yet another problem with Lau et al. is that the panel tester and grader does not provide a mechanism to measure the thickness of each panel tested with a high degree of accuracy. As explained in Lau et al., a thickness value for the panels is needed in order to calculate the strength and stiffness values for the panels. In the preferred embodiment of Lau et al., a nominal thickness value for a set of panels (see, e.g., TABLES I and II therein and the description thereof) is simply inputted into the microprocessor, so that the appropriate calculations can be made. As noted, Lau et al. do teach that if a more accurate calculation of strength and stiffness is desired, a thickness sensor such as a laser sensor or an ultrasonic sensor may be used to measure the actual thickness instead of using the nominal thickness of each panel. Even so, what Lau et al. fail to recognize, and what has been determined according to the present invention, is that the thickness of each panel is a very significant parameter in determining the most precise measure of the strength and stiffness value for each tested panel. For example, a laser sensor will only measure the thickness of a panel at the specific location where the laser contacts the panel. As can be appreciated by those skilled in the art, panels of the type described herein can have varying thicknesses over the length and width of each panel. A single laser sensor cannot take into account the varying thicknesses throughout the panels. As a result, the averaged thickness measurement obtained by a laser sensor may not be a true representative measurement of the overall thickness of the particular panel. It is possible that multiple laser sensors could be used to improve the accuracy of the averaged thickness measurement for each panel, but multiple sensors would add undesirable cost and complexity to the overall panel tester, thereby resulting in a less than optimum machine. Likewise, an ultrasonic sensor will simply not provide accurate thickness measurements. As can be appreciated by those skilled in the art, panels of the type described herein have a tendency to vibrate as they are processed along the continuously operating panel tester and grader. Such vibrations in the panels will undoubtedly adversely affect the readings taken by an ultrasonic thickness tester. Thus, according to the present invention, it has been determined that in order to obtain a more accurate calculated strength and stiffness value for each panel, a new and improved thickness measuring device is required.

In sum, what is needed is a panel tester and grader that improves on the apparatus and method described in Lau et al., thereby providing a more accurate account of the strength and stiffness properties of each panel tested.

SUMMARY OF THE INVENTION

The present invention provides a panel tester for testing individual panels delivered to the panel tester in a stream. The panel tester comprises a main frame including a plurality of rollers and defining a substantially S-shaped testing path. A substantially linear bypass path extends below the testing path. A bypass assembly is coupled to the main frame and is operable to move the main frame between a testing position in which panels are received by the testing path, and a bypass position in which panels are received by the bypass path.

According to another aspect of the present invention, the panel tester includes at least one sensor operatively coupled to a roller to measure a load applied to the roller. As the panel moves along the testing path, the load changes. A control system is provided and communicates with the sensor to monitor the load. As the panel moves along the testing path and the load changes, the control system detects the changes in the load and selectively records the load in response to the detected load changes. Specifically, the testing path includes substantially linear portions, and substantially curved portions, and as the panel moves from a linear portion to a curved portion of the testing path, the load increases. As a result of the load increasing, the control system begins recording the load. Similarly, when the panel moves from a curved portion to a linear portion of the testing path, the load decreases, and in response to the load decreasing, the control system ceases recording the load.

In a preferred embodiment, the bypass assembly includes a lifter assembly that lifts the main frame to the bypass position. When the main frame is in the bypass position, the lifter assembly and the bypass frame support the main frame. The main frame includes a conveyor assembly that substantially defines the bypass path and the bypass path extends below the testing path.

The present invention also provides a method for testing individual panels having a leading edge and delivered to a panel tester in a stream. The method includes guiding an individual panel through the panel tester along a substantially S-shaped testing path that is defined by a plurality of rollers. A load cell providing a load output is coupled to a deflector roller to measure a load applied to the panel by the deflector roller. The load output is monitored as the panels are guided through the panel tester. The leading edge of the panel is fed along the S-shaped path in a generally linear direction and the panel is bent by diverting the leading edge of the panel into a nip defined between two adjacent rollers. As the panel is bent, the panel engages the deflector roller and the load output increases. When the load output increases, the load output is recorded by a control system, and when the panel disengages the deflector roller and the load output decreases, the control system ceases recording the load.

Other features and advantages of the invention will become apparent to those skilled in the art upon review of the following detailed description, claims and drawings in which like numerals are used to designate like features.

BRIEF DESCRIPTION OF THE DRAWINGS

FIG. 1 illustrates a side elevational view of a panel tester and grader embodying the the present invention.

FIG. 2 is a section view taken along line 2—2 of FIG. 1.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein are for the purpose of description and should not be regarded as limiting.

DETAILED DESCRIPTION OF THE PREFERRED EMBODIMENT

FIG. 1 illustrates an in-line panel tester and grader 10 embodying the present invention wherein a composite panel 12 moves through the tester 10 in an "S" shaped path. Since the present invention is intended to provide certain improvements over the apparatus and method described in Lau et al., a complete description regarding many of the details of the apparatus 10 is not needed. Reference can be made to Lau et al. for a more complete description of the nonessential components of the apparatus and method according to the present invention. However, it should be noted that, like Lau et al., it is envisioned that the present invention may mark the end-use stiffness and strength figures on each panel and the present invention may also grade panels identifying rejects which can be discarded. In addition, it is envisioned that the panels may be sorted out into different grade bins thereby identifying premium quality panels and lesser quality panels. Lau et al. describes one method of calculating an end-use strength and stiffness value for each tested panel, which the present invention can employ. Moreover, as will be evident below, the present invention is also capable of use in other panel testing and grading systems wherein the end-use strength and stiffness value is based at least in part on the thickness of each panel and/or on the deflection for a specific load or the load for a particular deflection. As such, even though the present invention is described as having many improvements over Lau et al., it should be appreciated that the apparatus and method described herein is capable of use in other panel testers and graders according to the principles of the present invention. The present invention is directed toward improving the accuracy and reliability of data used to determine the end-use strength and stiffness value for each tested panel, such as, for example, the applied load for a particular deflection and the actual thickness for each panel. Thus, the present invention can be used in other situations where similar improvements are desired.

With reference to FIG. 1, a pair of cooperating in-feed guide rolls 14 and 18 guide the panel 12 past a first pair of spaced apart positioning rolls 21 and 22, each of which cooperate with a reaction roll 25 and 26 respectively to clamp the panel 12 therebetween and position the panel 12 against the reaction rolls 25, 26. A first deflector roll 30 is positioned generally midway between the rolls 21, 22 and functions to bend the panel 12 in a first direction along a first curved portion 34 of the "S" shaped path 36.

The panel 12 then passes and is guided by a second pair of spaced apart positioning rolls 37 and 38 each of which cooperates with a reaction roll 41 and 42 respectively, to clamp the panel 12 therebetween. A second deflector roll 46 is positioned generally midway between the second pair of positioning rolls 37, 38 and bends the panel 12 in a second direction along a second curved portion 50 of the "S" shaped path. The panel 12 then exits through a pair of cooperating out-feed guide rolls 54 and 58. The deflector rolls 30 and 46 are at least partially supported by load cells 59, one load cell 59 being positioned on each end of each deflector roll 30, 46. The load cells 59 send signals corresponding to the amount of load being applied to the panel 12 to further processing equipment. The load cells 59 may be any type of load cell commonly known to those skilled in the art which functions according to the principles of the present invention. A temperature sensor 60, which may be any suitable sensor known to those skilled in the art, senses the temperature of the panel 12 being tested and sends a signal to the further processing equipment which corresponds to the temperature of the panel 12 being tested.

The positioning of the guide rolls 14, 18, 54 and 58, positioning rolls 21, 22 and 37, 38, reaction rolls 25, 26 and 41, 42, and deflector rolls 30 and 46 are all suitably controlled by a computer or microprocessor (not shown) operatively connected thereto. The microprocessor suitably utilizes the information from the load cells, the temperature sensor, and the data concerning the make-up and size of each panel to calculate the end-use strength and stiffness properties for each panel as such is described, for example, in Lau et al. Such information may be shown on a computer screen or printed by a printer. In any event, the microprocessor is of a suitable type that is capable of receiving, interpreting and analyzing the necessary information to output the desired results.

The panel tester and grader 10 includes a main frame 62 which has three subframes therein. A first loading frame 66 supports the first deflector roll 30 and the two lower positioning rolls 21, 22. A second loading frame 70 supports the second deflector roll 46 and the two upper positioning rolls 37, 38. A third subframe 74 supports the lower reaction rolls 41, 42 as well as the second loading frame 70. The upper reaction rolls 25, 26 are supported directly by the main frame 62.

The in-feed guide rolls 14 and 18 are supported by an "L" shaped arm 78 which is pivotally mounted on the axis of rotation 80 of the adjacent reaction roll 25. A second "L" shaped arm (not shown) is positioned at the other ends of the rolls 14 and 18, such that reference to one can be viewed as reference to the other. The angular position of the arm 78 is adjusted by an electromechanical actuator 82 that pivots the arm 78 about the axis 80 of roll 25. The position of arm 78 is preferably predetermined based on the intended travel path for the panel 12 through the machine 10. The microprocessor is operatively coupled to the actuator 82 for controlling the location of the arm 78. Although the actuator 82 may be one of many different types of actuators capable of performing the desired functions, a linear actuator sold under the name of Warner Electrak 100, by Warner Electric of South Beloit, Ill., is particularly well suited for use according to the principles of the present invention.

The bottom in-feed guide roll 18 is connected to an electromechanical actuator 86 having a spring mount. The spacing between the top in-feed guide roll 14 and the bottom in-feed roll 18 is adjusted by the electromechanical actuator 86 which moves roll 18 the required amount depending on the general thickness of the panel to be tested. The microprocessor is operatively coupled to the actuator 86 for controlling the location of the roll 18 relative to roll 14. As will be further explained below, the spring mount of the actuator 86 allows the cooperating rolls 14 and 18 to accommodate panels passing therebetween which are of varying thicknesses. Although the actuator 86 may be one of many different types of actuators capable of performing the desired functions, a linear actuator similar to actuator 82 would be suitable.

The position of arm 78 is determined in one aspect on the position of the first deflector roll 30 which determines the degree of bending of the panel 12 in the first curved position 34 of the "S" shaped path. The panel 12 passes over the pair of rolls 21, 22 and is deformed by the roll 30 which causes the panel 12 to be pressed against the reaction rolls 25, 26 thereby causing the panel 12 to bend. As the panel is fed into the device and the leading edge of the panel 12 passes over the deflector roll 30, its direction of travel will not intersect with a nip 87 between the cooperating rolls 22 and 26. In this respect, the leading edge first travels along a substantially linear path through the first curved portion 34. In order to bend the panel 12, a deflector 90 is provided that diverts the leading edge of the panel 12 into the nip 87, thereby engaging the panel with the deflector roll 30. As illustrated, the deflector 90 extends generally upwardly and away from the roll 25, passes over the deflector roll 30, and extends generally downwardly toward the roll 26. The deflector 90 includes a downwardly facing, substantially planer leading edge guide surface 91 that is substantially tangent to the roll 26 to guide the leading edge of the panel smoothly toward the nip 87 and between the rolls 22 and 26. A trailing edge guide surface 92 is provided adjacent the roll 25 to guide the trailing edge of the panel as it is released from the rolls 21, 25. The trailing edge guide surface 92 is slightly offset from a tangent to the roll 25 to allow a slight amount of "springback" of the panel as the trailing edge is released from the rolls 21, 25 for reasons discussed further below.

The first deflector roll 30 is mounted on the first loading frame 66 with an arm 94 that is pivotally mounted on the frame 66. The position of the roll 30 relative to the frame 66 in the vertical direction can be determined in any number of different ways, one such way being described, for example, in Lau et al. The roll 30 is generally positioned at a selected distance above the horizontal plane defined by the upper portions of the outer peripheries of the two spaced-apart rolls 22 so as to impose the desired degree of bending to the panel 12 being tested. As illustrated, the roll 30 and the arm 94 are partially supported by the load cells 59.

To provide accurate data collection, the load cells 59 are constantly monitored by the microprocessor, however the recording of load cell data used for strength and stiffness calculations is intermittent. As the leading edge of the panel enters the first curved portion 34 of the load zone, there is a period of time where the panel is between the rolls 21, 25 but is not engaged with the deflector roll 30 or the rolls 22, 26. This is because of the upwardly inclined path along which the panel enters the first curved portion 34. During the period of time when the panel is not engaged with the deflector roll 30, the load cell 59 reading is substantially zero (assuming the mass of the deflector roll 30 and corresponding mounting components has been accounted for). As the leading edge continues through the first curved portion 34, the leading edge impacts the leading edge guide surface 91 of the deflector 90, which guides the leading edge into the nip 87, thereby bending the panel and bringing the panel into engagement with the deflector roll 30. As the panel 12 is bent and engages the deflector roll 30, the load cell reading "spikes" or rapidly and dramatically increases. This spike is recognized by the microprocessor, which as mentioned above constantly monitors the load cell reading, and the microprocessor begins recording load data that is subsequently used for the strength and stiffness calculations. Once the panel has traveled through the first curved section 34, recording of the load data is halted in a similar way. Specifically, when the trailing edge of the panel travels through the rolls 21, 25 and is subsequently released, the panel springs back due to the configuration of the trailing edge guide surface 92 described above. As the panel springs back, the load cell reading "falls off" or rapidly and dramatically decreases. This falling off is similarly recognized by the microprocessor, which then truncates the load data at a point in time immediately before which the trailing edge of the panel was released from the rolls 21, 25. The progression of the panel through the second curved path 50 is monitored and data recording is controlled in substantially the same way.

Pneumatic cylinders 98 are supported by the main frame 62 and are connected to the first loading frame 66. There are a total of four cylinders 98, one for each corner of frame 66. The cylinders 98 control the vertical movement of the frame 66 and are configured to provide a force that urges the frame 66 upwardly against a mechanical stop (not shown), thereby establishing a preset gap width between the cooperating rolls 21, 25 and 22, 26. The preset gap between each pair of cooperating rolls 21, 25 and 22, 26 may remain substantially the same regardless of the thickness of the panel to be tested, and is preferably slightly smaller than the thickness of the thinnest panel to be tested. The mechanical stops are also preferably adjustable to provide adjustment of the preset gap width if such adjustment is desired. The cylinders 98 fluidly communicate with a source of pressurized fluid via a pressure regulator 99. The pressure regulator 99 is used to regulate the pressure of the fluid supplied to the cylinders 98. In this way, the magnitude of the force provided by the cylinders 98 that urges the frame 66 upwardly is controllable such that when a panel 12 passes between the positioning rolls 21, 22 and reaction rolls 25, 26, the cylinders 98 are substantially resilient and compressible, thereby allowing the gap width to increase based upon the size of the panel. The configuration of the air cylinders 98 is also such that the cylinders 98 compensate for variations in the thickness of an individual panel 12 and maintain the pairs of cooperating rolls 21, 25 and 22, 26 in contact with the adjacent faces of the panel 12 being tested. As mentioned above, the preset gap width may remain substantially the same regardless of the thickness of the panel being tested, thereby reducing the need to adjust the gap width for the testing of panels 12 of different thicknesses. Although the cylinders 98 may be one of many different types of cylinders capable of performing the desired functions, the 'TA' series TRD Cylinders available from Bimba Manufacturing Company of Monee, Ill., are particularly well suited for use according to the principles of the present invention.

Turning now to the second curved portion 50, the subframe 74 is moved up or down depending upon the required "S" shaped configuration by electromechanical actuators 102, although other suitable positioning devices may be employed. Actuators 102 are supported by the main frame 62 and connected to the subframe 74. There are a total of four actuators 102, one for each corner of the subframe 74. One example of a suitable actuator is sold under the part number EC2S32T-5004A-50-MSZ-MT1E, by Industrial Device Corporation of Novato, Calif., other actuators may also be used.

The second loading frame 70 is carried on the subframe 74 and is movable up or down therewith. The second loading frame 70 is substantially the same as the first loading frame 66, but is inverted with the second deflector roll 46 pushing downwardly on the panel between the two positioning rolls 37, 38 which cooperate with reaction rolls 41, 42. The second deflector roll 46 is mounted on frame 70 in much the same fashion as deflector roll 30 is mounted on frame 66. As shown, an electromechanical actuator 106 may be used independently or in connection with a step cam 107 to vertically maneuver the roll 46 with respect to frame 70, although the roll 46 may be positioned relative to the frame 70 in any number of different ways suitable for use with the present invention. Electromechanical actuators 110 intercoupled between the loading frame 70 and the subframe 74. The actuators 110 are placed in each corner of frame 70 in order to move the frame 70 in a vertical direction with respect to the subframe 74. Such actuators 110 are similar to the actuators 102. As discussed above with respect to the cooperating rolls 21, 25 and 22, 26, a pre-set gap width is established between cooperating rolls 37, 41 and 38, 42 by adjusting the actuators 110 appropriately. To account for variations in panel thickness, the actuators 110 include springs 112 between the actuator and the loading frame 70 such that the rolls 37, 38 may deflect as a panel passes between the cooperating rolls 37, 41 and 38, 42. It should be appreciated that because the roll 46 is beneath the frame 70, the roll 46 will be mounted in a suitable manner to prevent it from falling out of position. In alternative embodiments, the actuators 110 may be replaced by pneumatic cylinders, similar to the pneumatic cylinders 98.

A deflector 114, similar to the deflector 90, is provided to guide the leading edge of the panel 12 toward the last positioning roll 38 in the second curved portion 50 in much the same way deflector 90 guides the leading edge of the panel 12 toward the last positioning roll 22 in the first curved portion 34. The deflector 114 also guides the trailing edge of the panel away from the positioning roll 37 in substantially the same manner as the deflector 90 guides the trailing edge away from the roll 21.

To exit the machine 10, the panel 12 passes from between the last positioning roll 38 and last reaction roll 42 and then from between the out-feed guide rolls 54 and 58. Guide rolls 54 and 58 are mounted on a pair of "L" shaped arms 118 (only one shown) in much the same way as in-feed guide rolls 14 and 18 are mounted on arms 78. Arm 118 is pivotally mounted on the axis of rotation 122 of the adjacent reaction roll 42. The angular position of the arm 118 is adjusted by an electromechanical actuator 126 that pivots the arm 118 around the axis 122 of roll 42. The position of arm 118 is preferably predetermined based on the intended travel path for the panel 12 through the machine 10. The microprocessor is operatively coupled to the actuator 126 for controlling the location of the arm 118. Actuator 126 is preferably of the same type as actuator 82. The top out-feed guide roll 54 is connected to an actuator 119, which is like actuator 86, and is operable in a similar way.

As in Lau et al., during movement through the "S" shaped path, forces are applied to each panel by the deflector rolls 30 and 46 and their reaction rolls 25, 26 and 41, 42 respectively, against which the panel is positioned by the positioning rolls 21, 22 and 37, 38 respectively. The in-feed guide rolls 14 and 18 and the out-feed guide rolls 54 and 58 ensure that the panel 12 maintains a substantially linear trajectory as the panel enters and exist the machine, such that substantially no additional forces are applied to the panel that might disturb the loading applied in the curved portions 34, 50. Unlike Lau et al., the present invention eliminates the first in-feed roll (40) and last out-feed roll (70) to substantially ensure that there are no bending forces applied to the panel 12 outside of the "S" shaped load zone.

The actuators, in conjunction with the microprocessor, move the appropriate framework to position all of the rolls in a preset position based on the general size of the panels to be tested. Once the rolls are properly positioned, a panel is passed through the testing machine, which monitors the load cells to measure the applied load for the particular deflection of the panel. The output of the temperature sensor is also monitored to sense the temperature of the panel. A panel thickness-measuring device 170 also measures the thickness of each panel. The panel thickness measuring device 170 is positioned relative to the framework 70 and 74 in order to provide a measurement of the thickness of each panel as the panels are fed through the machine. Although the device 170 is shown in the second curved portion 50 (FIG. 1), it should be understood that the device 170 or a second device in addition to device 170 could be placed in the first curved portion 34. The load, temperature and thickness values, among other things, are utilized by the microprocessor to determine the strength and stiffness values for each panel at ambient or end-use temperature. Lau et al. describes one algorithm that may be used to calculate such a value, although other algorithms may be used in accordance with the present invention.

The illustrated thickness-measuring device 170 is in the form of a proximity sensor. The proximity sensor includes a sensor 186 and a target 190. The sensor 186 is mounted to the subframe 74 and the target 190 is mounted to the second loading frame 70. As the panel passes between the cooperating rolls 37, 41 and 38, 42, the loading frame 70 deflects due to the resiliency provided by the springs 112. The sensor 186 is operable to detect the distance between the sensor 186 and the target 190, which varies as the panel passes through the second curved portion 50, and relays such information to the microprocessor for the strength and stiffness calculations. In other embodiments, a linear encoder or an LVDT may be used in a similar manner as the proximity sensor to determine the panel thickness.

As previously explained, the panel 12 travels between the positioning rolls and reaction rolls during the bending and loading process of the panel tester. When the panel 12 is located between the respective rolls, the gap between the opposing rolls is substantially equal to the thickness of the panels. This gap varies for each panel as the thickness of each panel varies. The pneumatic cylinders and spring-mounted actuators attached to the respective frames allow the gap to vary so the panels are not damaged as they pass between the opposing rolls. As the framework 70 moves up and down relative to the framework 74, the microprocessor records all of the thickness measurements provided by the thickness measuring device 170 and averages the measurements to obtain an average thickness value. This thickness value is then used by the microprocessor in computing the final strength and stiffness values for the panel.

The device 170 provides an accurate measure of the thickness of each panel 12, which may vary even between panels 12 that are manufactured to be the same thickness. The measurements taken by the device 170 provide more accurate strength and stiffness values compared to prior devices which relied merely on the intended manufacturing thickness value. The device 170 is capable of picking up most, if not all, of the variations or aberrations in a panel which could affect the average thickness value for each panel.

Positioned beneath the main frame 62 is a panel bypass system 200. The bypass system 200 is provided such that panels, which are fed to the device 10 in a stream from other panel processing equipment, may be conveyed along a substantially linear bypass path 204 instead of the S-shaped path 36. In this respect, panels that do not require testing are not subjected to unnecessary bending during the manufacturing process. Also, if the various rollers, frames, or actuators of the device should require maintenance, such maintenance may be performed without interrupting the production flow of the panels.

The bypass system 200 includes a bypass frame 208, a lifter in the form of a hydraulic ram 212, and a conveyor assembly 216 that generally defines the bypass path 204. The bypass frame 208 includes four substantially rectangular bypass legs 220 that are positioned just inwardly of main frame legs 224. The main frame legs 224 are slidably coupled to the bypass legs 220 by way of linear bearings 228. Referring also to FIG. 2, the main frame legs 224 each include a generally cylindrical rail 232 that is received by a respective linear bearing 228, each linear bearing 228 being coupled to a respective bypass leg 220. The bypass frame 208 also includes frame members 236 that further support the bypass legs 220 and generally strengthen the bypass frame 208. The conveyor assembly 216 includes a plurality of rollers 240 and is secured to the main frame 62.

In operation, the hydraulic ram 212 is extended and engages the main frame 62. Further extension of the ram 212 lifts the main frame 62 and the conveyor assembly 216 upwardly, while the cooperation of the rails 232 and the linear bearings 228 slidably guides the main frame legs 224, thereby stabilizing the main frame 62. The main frame 62 is lifted until the conveyor assembly 216 reaches a bypass position where the bypass path 204 is positioned to receive the stream of panels 12 from the upstream processing equipment, and to further convey the stream of panels toward downstream processing equipment. In this respect, the production of panels 12 may continue without the panels 12 passing through the S-shaped testing path 36. When it is again desired to test the panels 12 by guiding the panels 12 along the S-shaped path, the ram 212 is retracted until the main frame is lowered to a position where the S-shaped testing path 36 is positioned to receive the stream of panels from the upstream processing equipment, and to further convey the stream of panels toward the downstream processing equipment. The loading frames 66, 70 and the subframe 74 may then be repositioned as required for precise positioning to receive and test the panels 12.

The foregoing description of the present invention has been presented for purposes of illustration and description. Furthermore, the description is not intended to limit the invention in the form disclosed herein. Consequently, variations and modifications commensurate with the above teachings in skill or knowledge of the relevant art, are within the scope of the present invention. The embodiments described herein are further intended to explain the best modes known for practicing the invention and to enable others skilled in the art to utilize the invention as such, or other embodiments and with various modifications required by the particular applications or uses of the present invention. It is intended that the appended claims are to be construed to include alternative embodiments to the extent permitted by the prior art.

Various features of the invention are set forth in the following claims.

What is claimed is:

1. A panel tester for testing individual panels delivered to the panel tester in a stream, the panel tester comprising:
   a main frame including a plurality of rollers, the main frame defining a substantially S-shaped testing path;
   a substantially linear bypass path extending below the testing path; and
   a bypass assembly coupled to the main frame and operable to move the main frame between a testing position wherein panels are received by the testing path, and a bypass position wherein panels are received by the bypass path.

2. The panel tester of claim 1, wherein the bypass assembly includes a lifter assembly that lifts the main frame to the bypass position.

3. The panel tester of claim 2, wherein the bypass assembly includes a bypass frame, and wherein the main frame is slidably coupled to the bypass frame.

4. The panel tester of claim 3, wherein when the main frame is in the bypass position, the main frame is supported by the lifter and the bypass frame.

5. The panel tester of claim 1, wherein the main frame includes a conveyor assembly substantially defining the bypass path.

6. A panel tester for testing individual panels delivered to the panel tester in a stream, the panel tester comprising:
   a main frame supporting a plurality of rollers, the main frame at least partially defining a substantially S-shaped testing path and a substantially linear bypass path;
   a bypass assembly including a bypass frame slidably coupled to the main frame, the bypass assembly operable to move the main frame between a testing position wherein panels are received by the testing path, and a bypass position wherein panels are received by the bypass path.

7. The panel tester of claim 6, wherein the bypass assembly includes a lifter assembly that lifts the main frame to the bypass position.

8. The panel tester of claim 7, wherein when the main frame is in the bypass position, the main frame is supported by the lifter assembly and the bypass frame.

9. The panel tester of claim 1, wherein the main frame includes a conveyor assembly substantially defining the bypass path.

10. The panel tester of claim 1, wherein the bypass path extends below the testing path.

11. A panel tester for testing individual panels delivered to the panel tester in a stream, the panel tester comprising:

a main frame including a plurality of rollers, the rollers being positioned to guide the panels along a substantially S-shaped testing path;

at least one sensor operatively coupled to a roller to measure a load applied to the roller, the load changing based upon a position of the panel along the testing path; and a control system communicating with the sensor to monitor the load, the control system selectively recording the load in response to a detected load change.

12. The panel tester of claim 11, wherein the control system is operable to translationally move at least some of the rollers with respect to the main frame.

13. The panel tester of claim 11, wherein the testing path includes substantially linear portions, and substantially curved portions.

14. The panel tester of claim 13, wherein in response to the panel moving from a linear portion to a curved portion of the testing path, the load increases, and wherein in response to the load increasing, the control system begins recording the load.

15. The panel tester of claim 13, wherein in response to the panel moving from a curved portion to a linear portion of the testing path, the load decreases, and wherein in response to the load decreasing, the control system ceases recording the load.

16. A method for testing individual panels delivered to a panel tester in a stream, the individual panels having a leading edge, the method comprising:

guiding an individual panel through the panel tester along a substantially S-shaped testing path, the testing path defined by a plurality of rollers;

coupling a load cell to a deflector roller to measure a load applied to the panel by the deflector roller, the load cell providing a load output;

monitoring the load output as the panels are guided through the panel tester;

feeding the leading edge of the panel along the S-shaped path in a generally linear direction;

bending the panel by diverting the leading edge of the panel into a nip between two rollers, thereby engaging the panel with the deflector roller and increasing the load output; and recording the load output in response to the load output increasing.

17. The method of claim 16, further comprising releasing a trailing edge of the panel from between two rollers, thereby disengaging the panel with the deflector roller and decreasing the load output, and terminating recording of the load output in response to the load output decreasing.

18. The method of claim 16, wherein guiding an individual panel along an S-shaped path comprises guiding the panel along a first curved portion and a second curved portion.

19. The method of claim 16, wherein monitoring the load output comprises sending signals from the load cell to a control system.

\* \* \* \* \*